US009884025B2

(12) United States Patent
Maio

(10) Patent No.: US 9,884,025 B2
(45) Date of Patent: *Feb. 6, 2018

(54) MICROSPHERES OF PANCREATIC ENZYMES WITH HIGH STABILITY AND PRODUCTION METHOD THEREOF

(71) Applicant: APTALIS PHARMA S.R.L., Pessano con Bornago (IT)

(72) Inventor: Mario Maio, Tivoli (IT)

(73) Assignee: APTALIS PHARMA S.R.L. (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/953,638

(22) Filed: Nov. 30, 2015

(65) Prior Publication Data
US 2016/0120815 A1    May 5, 2016

Related U.S. Application Data

(63) Continuation of application No. 10/416,702, filed as application No. PCT/EP01/13115 on Nov. 13, 2001, now Pat. No. 9,259,393.

(30) Foreign Application Priority Data

Nov. 15, 2000    (IT) .............................. MI2000A2456

(51) Int. Cl.
 *A61K 9/50*    (2006.01)
 *A61K 9/16*    (2006.01)
 (Continued)

(52) U.S. Cl.
 CPC .............. *A61K 9/50* (2013.01); *A61K 9/1641* (2013.01); *A61K 9/5047* (2013.01); *A61K 38/54* (2013.01); *C12N 11/08* (2013.01)

(58) Field of Classification Search
 CPC ...... A61K 9/50; A61K 9/1641; A61K 9/5047; A61K 38/54; C12N 11/08
 See application file for complete search history.

(56) References Cited

U.S. PATENT DOCUMENTS 3,844,891 A    10/1974  Hess et al.
4,079,125 A    3/1978   Sipos
(Continued)

FOREIGN PATENT DOCUMENTS

CA    2263703 A1    8/1999
CA    2419572 A1    8/2004
(Continued)

OTHER PUBLICATIONS

Polysciences, Inc. "PEG 4000, EM Grade: Technical Data Sheet 279" published Oct. 1999, 2 pgs.*
(Continued)

*Primary Examiner* — Thane Underdahl
(74) *Attorney, Agent, or Firm* — Carter, DeLuca, Farrell & Schmidt, LLP

(57) ABSTRACT

The present invention refers to new microspheres including pancreatic enzymes, pharmaceutical compositions containing them, and a process to obtain them. The process here described doesn't involve the use of solvents and proves to be remarkably shorter and efficient than the producing methods of the prior arts. The microspheres obtained, including one or more pancreatic enzymes, one or more hydrophilic low-melting polymers and eventual excipients, have an high enzymatic activity, bio-availability and stability.

12 Claims, 1 Drawing Sheet

Figure 1A:
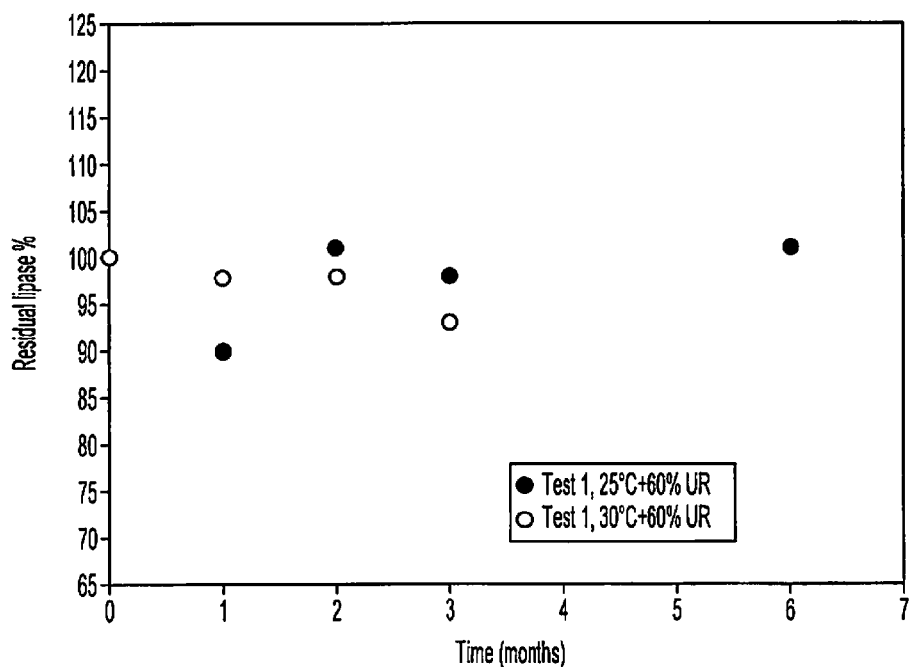

(51) Int. Cl.
*A61K 38/54* (2006.01)
*C12N 11/08* (2006.01)

(56) References Cited

U.S. PATENT DOCUMENTS

| | | | |
|---|---|---|---|
| 4,237,229 A | 12/1980 | Hartdegen et al. |
| 4,280,971 A | 7/1981 | Wischniewski et al. |
| 4,447,412 A | 5/1984 | Bilton |
| 4,704,295 A | 11/1987 | Porter et al. |
| 4,786,505 A | 11/1988 | Lovgren et al. |
| 4,849,227 A | 7/1989 | Cho |
| 4,859,471 A | 8/1989 | Fulberth et al. |
| 5,225,202 A | 7/1993 | Hodges et al. |
| 5,260,074 A | 11/1993 | Sipos |
| 5,306,506 A | 4/1994 | Zema et al. |
| 5,324,514 A | 6/1994 | Sipos |
| 5,378,462 A * | 1/1995 | Boedecker ........... A61K 9/1641 |
| | | | 424/408 |
| 5,460,812 A | 10/1995 | Sipos |
| 5,570,104 A | 10/1996 | Hayashi |
| 5,578,304 A | 11/1996 | Sipos |
| 5,665,428 A | 9/1997 | Cha et al. |
| 5,733,575 A | 3/1998 | Mehra et al. |
| 5,733,763 A | 3/1998 | Markussen et al. |
| 5,750,104 A | 5/1998 | Sipos |
| 5,861,177 A | 1/1999 | Atzl et al. |
| 5,861,291 A | 1/1999 | Abboudi et al. |
| 6,051,220 A | 4/2000 | Scharpe |
| 6,313,102 B1 | 11/2001 | Colaco et al. |
| 6,318,650 B1 | 11/2001 | Breitenbach et al. |
| 6,352,974 B1 | 3/2002 | Ghirri et al. |
| 6,426,091 B1 | 7/2002 | Okumura et al. |
| 6,607,747 B2 | 8/2003 | Ullah et al. |
| 6,855,336 B2 | 2/2005 | Chen et al. |
| 6,955,903 B2 | 10/2005 | Kulkarni et al. |
| 7,201,923 B1 | 4/2007 | van Lengerich |
| 7,658,918 B1 | 2/2010 | Ortenzi et al. |
| 8,071,089 B2 | 12/2011 | Schuler et al. |
| 8,221,747 B2 | 7/2012 | Ortenzi et al. |
| 8,246,950 B2 | 8/2012 | Ortenzi et al. |
| 8,293,229 B2 | 10/2012 | Ortenzi et al. |
| 8,562,978 B2 | 10/2013 | Ortenzi et al. |
| 8,562,979 B2 | 10/2013 | Ortenzi et al. |
| 8,562,980 B2 | 10/2013 | Ortenzi et al. |
| 8,562,981 B2 | 10/2013 | Ortenzi et al. |
| 8,784,884 B2 | 7/2014 | Perrett et al. |
| 2001/0024660 A1 | 9/2001 | Ullah et al. |
| 2001/0046493 A1 | 11/2001 | Margolin et al. |
| 2002/0044968 A1 | 4/2002 | van Lengerich |
| 2002/0054907 A1 | 5/2002 | Devane et al. |
| 2002/0187536 A1 | 12/2002 | Kulkarni et al. |
| 2004/0057944 A1 | 3/2004 | Galle et al. |
| 2004/0101562 A1 | 5/2004 | Maio |
| 2004/0121010 A1 | 6/2004 | Hirsh et al. |
| 2004/0197321 A1 | 10/2004 | Sipos et al. |
| 2004/0213847 A1 | 10/2004 | Matharu et al. |
| 2005/0019417 A1 | 1/2005 | Ko et al. |
| 2005/0158299 A1 | 7/2005 | Margolin et al. |
| 2005/0208133 A1 | 9/2005 | Tsutsumi et al. |
| 2005/0281876 A1 | 12/2005 | Li et al. |
| 2006/0121017 A1 | 6/2006 | Margolin et al. |
| 2006/0198838 A1 | 9/2006 | Fallon |
| 2007/0025977 A1 | 2/2007 | Mulberg |
| 2007/0141151 A1 | 6/2007 | Silver et al. |
| 2007/0148151 A1 | 6/2007 | Frink et al. |
| 2007/0148152 A1 | 6/2007 | Shlieout et al. |
| 2007/0190142 A1 | 8/2007 | Breitenbach et al. |
| 2008/0199448 A1 | 8/2008 | Ross et al. |
| 2008/0274174 A1 | 11/2008 | Ortenzi et al. |
| 2008/0279839 A1 | 11/2008 | Schuler et al. |
| 2008/0279953 A1 | 11/2008 | Ortenzi et al. |
| 2008/0299185 A1 | 12/2008 | Ortenzi et al. |
| 2009/0081184 A1 | 3/2009 | Margolin et al. |
| 2009/0117180 A1 | 5/2009 | Ortenzi et al. |
| 2009/0148545 A1 | 6/2009 | Falk et al. |
| 2009/0226414 A1 | 9/2009 | Tijssen et al. |
| 2009/0232789 A1 | 9/2009 | Fallon |
| 2010/0021537 A1 | 1/2010 | Ortenzi et al. |
| 2010/0239559 A1 | 9/2010 | Freedman et al. |
| 2010/0270183 A1 | 10/2010 | Ortenzi et al. |
| 2011/0064799 A1 | 3/2011 | Perrett et al. |
| 2011/0123605 A1 | 5/2011 | Ortenzi et al. |
| 2011/0123633 A1 | 5/2011 | Ortenzi et al. |
| 2011/0123634 A1 | 5/2011 | Ortenzi et al. |
| 2012/0177629 A1 | 7/2012 | Broussard et al. |
| 2012/0201875 A1 | 8/2012 | Ortenzi et al. |
| 2013/0251926 A1 | 9/2013 | Wood et al. |
| 2014/0170212 A1 | 6/2014 | Ortenzi et al. |
| 2014/0287035 A1 | 9/2014 | Perrett et al. |
| 2014/0295474 A1 | 10/2014 | Latino et al. |

FOREIGN PATENT DOCUMENTS

| | | |
|---|---|---|
| CN | 87103560 A | 5/1988 |
| CN | 1235824 A | 11/1999 |
| CN | 1376519 A | 10/2002 |
| CN | 1489476 A | 4/2004 |
| CN | 101430279 A | 5/2009 |
| DE | 2730481 A1 | 1/1978 |
| DE | 19907764 A1 | 11/1999 |
| EA | 201290985 A1 | 5/2013 |
| EP | 8780 A2 | 3/1980 |
| EP | 0035780 A1 | 9/1981 |
| EP | 0115023 A2 | 8/1984 |
| EP | 0256127 A1 | 2/1988 |
| EP | 0283442 A1 | 9/1988 |
| EP | 304332 A2 | 2/1989 |
| EP | 0576938 A1 | 1/1994 |
| EP | 0879772 A2 | 11/1998 |
| EP | 1010423 A2 | 6/2000 |
| EP | 1279402 A1 | 1/2003 |
| EP | 1335706 B1 | 4/2005 |
| EP | 1579771 A1 | 9/2005 |
| EP | 1931316 A2 | 6/2008 |
| EP | 1967211 A1 | 9/2008 |
| EP | 2079445 A2 | 7/2009 |
| EP | 2477645 A4 | 7/2012 |
| EP | 2621476 A1 | 8/2013 |
| EP | 2754437 A2 | 7/2014 |
| EP | 2818160 A1 | 12/2014 |
| ES | 489967 A | 10/1980 |
| FR | 2313916 A1 | 1/1977 |
| GB | 1509866 A | 5/1978 |
| JP | S52-3819 A | 1/1977 |
| JP | 58-085159 | 5/1983 |
| JP | H05-38731 A | 2/1993 |
| JP | 538731 | 10/1993 |
| JP | H05-76928 B2 | 10/1993 |
| JP | 10-295374 A | 11/1998 |
| JP | H11-514088 A | 11/1999 |
| JP | 2002506527 A | 2/2002 |
| JP | 2004-513645 A | 5/2004 |
| JP | 4187085 B2 | 11/2008 |
| JP | 2010519217 A | 6/2010 |
| KR | 100804096 B1 | 2/2008 |
| WO | 8705505 A1 | 9/1987 |
| WO | 90/09428 A1 | 8/1990 |
| WO | 9009440 A1 | 8/1990 |
| WO | 90/15856 A1 | 12/1990 |
| WO | 93/07859 A1 | 4/1993 |
| WO | 93/18753 A1 | 9/1993 |
| WO | 9325669 A1 | 12/1993 |
| WO | 9600773 A1 | 1/1996 |
| WO | 9746658 A1 | 12/1997 |
| WO | 98/01544 A1 | 1/1998 |
| WO | 97/46860 A3 | 2/1998 |
| WO | 98/58254 A1 | 12/1998 |
| WO | 01/25412 A1 | 4/2001 |
| WO | 01/70047 A1 | 9/2001 |
| WO | 0174980 A2 | 10/2001 |
| WO | 0240045 A2 | 5/2002 |
| WO | 02058735 A1 | 8/2002 |
| WO | 2004074470 A1 | 9/2004 |
| WO | 2005042012 A1 | 5/2005 |

(56) References Cited

FOREIGN PATENT DOCUMENTS

| WO | 2005092370 A1 | 10/2005 |
|---|---|---|
| WO | 2006044529 A1 | 4/2006 |
| WO | 2007013752 A1 | 2/2007 |
| WO | 2007020259 A2 | 2/2007 |
| WO | 2007020260 A2 | 2/2007 |
| WO | 08/017659 A1 | 2/2008 |
| WO | 2008102264 A2 | 8/2008 |
| WO | 2009109856 A2 | 9/2009 |
| WO | 2011035079 A1 | 3/2011 |
| WO | 2011072069 A2 | 6/2011 |
| WO | 2011114224 A1 | 9/2011 |
| WO | 2012019186 A1 | 2/2012 |
| WO | 2012042372 A1 | 4/2012 |
| WO | 2012052853 A2 | 4/2012 |
| WO | 2013021359 A1 | 2/2013 |
| WO | 2014141121 A1 | 9/2014 |
| WO | 2015/019198 A2 | 2/2015 |
| WO | 2015/020943 A2 | 2/2015 |
| WO | 2015069677 A1 | 5/2015 |
| WO | 2015193730 A1 | 12/2015 |

OTHER PUBLICATIONS

English Translation of Example 3 of Priority Document Italian Patent Application No. MI2000 A 0022456; (D21); 1 page.
Summary of facts and submissions, Grounds for the Decision (Annex)—opposition, corresponding to Application No. 01 994 654.0, dated Feb. 23, 2009; 9 pages.
Interlocutory Decision in Opposition proceedings, corresponding to Application No. 01 994 654.0-2107, dated Feb. 23, 2009; 2 pages.
Druckexemplar, relating to EP1 335 706 B1, 8 pages.
Provision of the minutes in accordance with Rule 124(4) EPC, dated Feb. 23, 2009, corresponding to Application No. 01 994 654.0-2107; 12 pages.
Non-patent literature, dated Jul. 30, 2012, relating to the Appeal Procedure, (Eisenfuhr Speiser); 7 pages.
Letter from Botti & Ferrari, dated Jun. 27, 2012, relating to the Appeal Procedure, 10 pages.
Non-patent literature cited during the Appeal Procedure, (Eisenfuhr Speiser), Grounds of Appeal, dated Jun. 30, 2009; 24 pages.
Letter from Botti & Ferrari, dated Sep. 18, 2009, relating to the Appeal Procedure, 15 pages.
Main Request, Claims with revisions, relating to Appeal Procedure; 1 page.
Description, relating to EP 1 335 706, relating to the Appeal Procedure; 1 page.
Main Request, Claims 1-7, relating to Appeal Procedure; 2 pages.
Royce, et al., Alternative Granulation Technique: Melt Granulation, Drug Development and Industrial Pharmacy, (D4) 22(9&10), 917-924; Copyright 1996 by Marcel Dakker, Inc.
Lombroso, "About the Destruction of the Pancreatic Enzymes by Means of Heat and the Substances that Hamper Such Action", Archivio di Farmacologia Sperimentale e Scienze Affini, Laboratory of Physiology of the R. University of Rome; 14 pages.
Inovozymes—Savinase, novozymes, Rethink Tomorrow, Annex 1, A Hard-working, robust protease used to remove protein-based stains; 1 page.
Notice of Opposition to a European Patent and opposition documents related to Patent No. EP 1 335 706 B1, (Opposition file history as of Jan. 14, 2009, excluding non-duplicative, non-administrative documents; (92 total pages).
Non-patent literature dated Sep. 30, 2011, relating to the Appeal Procedure, (Eisenfuhr Speiser); 2 pages.
Non-patent literature cited during the Appeal Procedure, (universitatbonn) (D23), dated Sep. 20, 2011; 15 pages.
Non-patent literature cited during the Appeal Procedure, (One Step Ahead, Granulation and drying for all types of products), Rotolab, (D24); 8 pages.

Sincero, et al., "Detection of hepatitis A virus (HAV) in oysters (*Crassostrea gigas*)" Water Research, Elsevier, Amsterdam, NL, vol. 40, No. 5, Mar. 1, 2006; pp. 896-902.
Langeveld, et al, "Inactivated recombinant plant virus protects dogs from a lethal challenge with canine parvovirus" Vaccine, Butterworth Scientific Guildford, GB, vol. 19, No. 27, Jun. 14, 2001, pp. 3661-3670.
Singh, et al., "Canine parvovirus-like particles, novel nanomaterial for tumor targeting" Journal of Nanobiotechnology 2006, vol. 4, No. 2, dated Feb. 13, 2006; 11 pages.
Shieh, et al., "A method to detect low levels of enteric virus in contaminated oysters", Applied and environmental Microbiology, vol. 65, No. 11, Nov. 1999, pp. 4709-4714.
Bergeron, et al., Genomic Organization and Mapping of Transcription and Translation Products of the NADL-2 Strain of Porcine Parvovirus, Virology, 1993, 197(1): pp. 86-98.
Bergeron, J., Hebert, B. and Tijssen, P. (1996), Genomic Organization of the Kresse Strain of Porcine Parvovirus: Identification of the Allotropic Determinant and Comprison with Those of NADL-2 and Field Isolates, Journal of Virology 70, pp. 2508-2515.
Simpson, et al., "The Structure of Porcine Parvovirus: Comparison With Related Viruses", J. Mol. Biol., 2002, 315(5); pp. 1189-1198.
Szelei, et al., "Porcine Parvovirus". In: Kerr, et al., eds, Parvoviruses, London: Hodder Arnold; 2006; pp. 434-445.
Canaan, et al., 2004, "Interfacial Enzymology of Parvovirus Phospholipases A2", Journal of Biologizal Chemistry 279(15), pp. 14502-14508.
Zadori, et al., 2001, "A Viral Phospholipase A2 is Required for Parvovirus Infectivity", Developmental Cell 1: pp. 291-302.
Zadori, et al., 2005, "SAT: a Late NS Protein of Porcine Parvovirus", Journal of Virology 79(20); pp. 13129-13138.
Mullendore, et al., Improved Method for the Recovery of Hepatitis A virus from oysters, Journal of Virological Methods 94, pp. 25-35 (2001).
Sair, et al., "Improved Detection of Human Enteric Viruses in Foods by RT-PCR", Journal of Virological Methods 100, pp. 57-69 (2002).
Guevremont, et al., "Development of an Extraction and Concentration Procedure and Comparison of RT-PCR Primer Systems for the Detection of Hepatitis A Virus and Norovirus GII in Green Onions", Journal of Virological Methods 134; pp. 130-135 (2006).
International Search Report and Written Opinion of the International Searching Authority, corresponding to International Aplication No. PCT/US14/49569, dated Nov. 14, 2014; 8 total pages.
US Pharmacopeia, Chapter 786, Particle Size Distribution Estimation by Analytical Sieving, Web download, Jun. 26, 2009; 5 pages.
Gohel, "A Review of Co-Processed Directly Compressible Excipients," J. Pharm. Pharmaceutical Sciences, 8(1); pp. 76-93; (2005).
Priority Document, Italian Patent No. MI2000 A 002456, 25 pages.
International Search Report, dated Jun. 23, 2014, corresponding to International Application No. PCT/IB2014/059722; 4 pages.
Ferrie, et al., "Pancreatic Enzyme Supplementation for Patients Receiving Enteral Feeds," Techniques and Procedures, Nutrition in Clinical Practice, vol. 26, No. 3, Jun. 2011; pp. 349-351.
Chen, et al., "Enteral Nutrition Formulas: Which Formula is Right for your Adult Patient," Invited Review, Nutrition in Clinical Practice, vol. 24, No. 3, Jun./Jul. 2009; pp. 344-355.
International Search Report and Written Opinion of the International Searching Authority, corresponding to International Application No. PCT/US14/63984, dated Mar. 13, 2015; 10 total pages.
International Search Report and Written Opinion of the International Searching Authority, dated Mar. 13, 2015, corresponding to International Application No. PCT/US14/63984; 9 total pages.
Canadian Office Action dated Mar. 18, 2015 and Canadian Examination Search Report dated Mar. 10, 2015, corresponding to Canadian Application No. 2,677,989; 4 total pages.
International Search Report and Written Opinion of the International Searching Authority, dated Mar. 2, 2015, corresponding to International Application No. PCT/IB2014/002583; 13 total pages.
Hwang, et al., "Selective Precipitation of Proteins From Pancreatin Using Designed Antisolvents", Industrial & Engineering Chemistry Research, vol. 46, No. 12, Jun. 1, 2007; pp. 4289-4294.

(56) References Cited

OTHER PUBLICATIONS

International Search Report, and Written Opinion of the International Searching Authority, corresponding to International Application No. PCT/US14/49569, dated Nov. 14, 2014; 8 total pages.
Queensland Government, "Tube Feeding at Home," Jan. 15, 2011, http://www.ausee.org/tube%20Feeding.pdf; 27 pages (Especially p. 13, Paragraph 3).
Wohlt, et al., "Recommendations for the Use of Medications with Continuous Enteral Nutrition," Am J Health Syst Pharm., 2009, 15 pages (Especially p. 4, Paragrah 7 and p. 5, Paragraph 1).
Singapore Search and Examination Report, dated Jan. 8, 2015, corresponding to Singapore Application No. 2012091583; 6 pages.
European Communication, dated Jan. 8, 2015, corresponding to European Patent Application No. 14176579.2; 2 pages.
Chinese First Office Action and Search Report (English translations), dated Apr. 3, 2015, corresponding to Chinese Patent Application No. 201410059861.7; 23 total pages.
Israeli Office Action dated May 10, 2015 (No English translation), corresponding to Israeli Patent Application No. 200407; 2 pages.
European extended Search Report, dated Jun. 2, 2015, corresponding to European Patent Application No. 14150794.7; 10 pages.
Japanese Office Action (No English translation), dated May 12, 2015, corresponding to Japanese Patent Application No. 2013-530811; 3 pages.
Canadian Office Action dated Jul. 3, 2015, corresponding to Canadian Patent Application No. 2,774,269; 4 pages.
Japanese Final Office Action (No English translation), dated Jul. 7, 2015, corresponding to Japanese Patent Application No. 2012-529909; 3 pages.
Chilean Office Action (without English Translation) dated Jul. 22, 2015, corresponding to Chilean Patent Application No. 00658-2012; 8 pages.
Communication of a Notice of Oppoistion to a European Patent Application and opposition documents related to Patent Application No. EP 117885223.3, dated Aug. 5, 2015 (678 total pages).
Chinese Office Action (No English translation available), dated Jul. 28, 2015, corresponding to Chinese Patent Application No. 201180055719.X; 13 pages.
Russian Office Action (with English translation), dated Jun. 15, 2015, corresponding to Russian Patent Appplication No. 2014104591/15; 10 total pages.
European Communication dated Jul. 6, 2015, corresponding to European patent application No. 14150794.7; 2 pages.
Korean Notice of Preliminary Rejection (with English translation), dated Jun. 12, 2015, corresponding to Korean patent application No. 10-2015-7004820; 16 total pages.
Australian Patent Examination Report No. 1, dated Jul. 6, 2015, corresponding to Australian Patent Application No. 2014203364; 4 pages.
Canadian Office Action and Examination Search Report dated Sep. 3, 2015, corresponding to Canadian Patent Application No. 2,677,989; 4 total apges.
Japanese Decision of Rejection (with English translation) dated Sep. 25, 2015, corresponding to Japanese Applcation No. 2013-265143; 9 total pages.
English translation of Chinese Second Office Action dated Dec. 21, 2015, corresponding to Chinese Application No. 201410059861.7; 5 pages.
Taiwanese Office Action (with English translation), dated Nov. 3, 2015, corresponding to Taiwanese Application No. 102138934; 16 total pages.
International Preliminary Report on Patentability and Written Opinion of the International Searching Authoirty, corresponding to International Application No. PCT/IB2014/059722, dated Sep. 15, 2015; 9 Pages.
Australian Patent Examination Report 1, dated Sep. 15, 2015, corresponding to Australian Patent Application No. 2014253526; 3 pages.

Eurasian Search Report (with English translation) issued by the EUrasian Patent Organization (EAPO) dated Sep. 16, 2015, corresponding to Eurasian Patent Application No. 201590836; 4 total pages.
Eurasian Search Report (with English translation) issued by the EUrasian Patent Organization (EAPO) dated Sep. 16, 2015, corresponding to Eurasian Patent Application No. 201590835; 4 total pages.
Ukrainian Office Action (with English Translation) dated Sep. 23, 2015, corresponding to Ukraine Application No. a 2013 03847; 11 total pages.
Colombian Office Action (No English Translation Available), dated Sep. 30, 2015, corresponding to Colombian Application No. 14-33910; 11 pages.
Japanese Office Action (with English translation), dated May 12, 2015, corresponding to Japanese Patent Application No. 2013-530811; 8 total pages.
International Search Report and Written Opinion of the International Searching Authority dated Nov. 20, 2015, corresponding to International Application No. PCT/IB2015/001237; 17 total pages.
Schielke et al., "Thermal Stability of Hepatitis E. Virus Assessed by a Molecular Biological Approach," Virology Journal, Biomed Central, vol. 8, No. 1, Oct. 31, 2011; 9 pages.
Eurasian Office Action (With English Translation) dated Oct. 30, 2015, correpsonding to Eurasian Application No. 201390409/28; 4 total pages.
English translation of Israeli Office Action dated Jan. 11, 2016, corresponding to Israeli Patent Application No. 225504; 3 pages.
Russian Office Action (with English translation), dated Oct. 29, 2015, corresponding to Russian Application No. 2014104591; 7 total pages.
Mesh to Micron Conversion Chart—Fluideng.com, Copyright 2002—Property of TM Industrial Supply, Inc.; (D20); http://www.fluideng.com/FE/meshmicron.html; Jun. 30, 2009; 1 page.
International Preliminary Report on Patentability and Written Opinion of the International Searching Authority, dated Jan. 26, 2016, corresponding to International Application No. PCT/IB2014/002583; 10 total pages.
European Search Report dated Jan. 22, 2016, corresponding to European Application No. 15178147.3; 9 pages.
Communication of the Board of Appeal, corresponding to Appeal No. T2255/12-3.3.07, dated Mar. 7, 2016; 11 pages.
Non-Patent Literature document—"Oppoistion against European Patent No. 1 931 316 in the anme of Abbott Products GmbH," correspnding to Appeal No. T2255/12-3.3.07, (letter from Botti & Ferrari, to the European Patent Office), dated May 13, 2013; 9 pages.
Non-Patent Literature document—"Notice of Appeal against the decision revoking the patent further to opposition proceedings," (from Cabinet Beau de Lomenie to the European Patent Office), corresponding to European Patent No. 1 931 316, dated Oct. 26, 2012; 1 page.
Non-Patent Literature document—"Grounds of Appeal", (from Cabinet Beau de Lomenie to the European Patent Office), corresponding to European Patent No. 1 931 316, dated Jan. 2, 2013; 10 pages.
Non-Patent Literature document—"Decision revoking the European Patent," issued by the European Patent Office, corresponding to European Patent No. 1 931 316, dated Sep. 5, 2012; 14 pages.
Non-Patent Literature document—"Persons attending oral proceedings on patentee's side," (from Cabinet Beau de Lomenie to the European Patent Office), corresponding to European Patent No. 1 931 316, dated May 2, 2012; 1 page.
Non-Patent Literature document—"Submission in opposition proceedings," issued by the European Patent Office, corresponding to European Patent No. 1 931 316, dated May 2, 2012; 1 page.
Non-Patent Literature document—"Reply to summons to attend oral proceedings; filing of new main claim request," (from Cabinet Beau de Lomenie to the European Patent Office), corresponding to European Patent No. 1 931 316, dated Feb. 23, 2012; 2 pages.
Non-Patent Literature document—"Submission in opposition proceedings," issued by the European Patent Office, corresponding to European Patent No. 1 931 316, dated Feb. 23, 2012; 2 pages.

(56) References Cited

OTHER PUBLICATIONS

Non-Patent Literature document—Letter from Europatent to European Patent Office, corresponding to European Patent No. 1 931 316, dated Feb. 6, 2012; 1 page.
Thoma et al., "Influence of aqueous coatings on the stability of enteric coated pellets and tablets," European Journal of Pharmaceutics and Biopharmaceutics, Elsevier, (D11), vol. 47(1), (1999); pp. 39-50.
Non-Patent Literature document—"Submission in opposition proceedings," issued by the European Patent Office, corresponding to European Patent No. 1 931 316, dated Jan. 11, 2012; 2 pages.
Non-Patent Literature document—"Inquiry concerning summons to oral proceedings," (from Cabinet Beau de Lomenie to the European Patent Office), corresponding to European Patent No. 1 931 316, dated Jan. 11, 2012; 1 page.
Non-Patent Literature document—"Brief Communication, Communication pursuant to Article 1(2) of the decision of the President of the EPO dated Jul. 12, 2007 concerning the filing of authorisations and Communication of amended entries concerning the representative," dated Sep. 20, 2011, issued by the European Patent Office, corresponding to European Patent No. 1 931 316; 3 total pages.
Non-Patent Literature document—"Notice of Opposition Filed by Eurand S.p.A.," (from Abbott Products GmbH), corresponding to European Patent No. 1 931 316, dated Jun. 7, 2011; 6 pages.
Non-Patent Literature document—"Notice of Opposition against the European Patent EP-B-1 931 316", (letter from Botti & Ferrari to the European Patent Office), dated Nov. 15, 2010, 12 pages.
Colombian Office Action (No English translation available), dated Feb. 19, 2016, corresponding to Colombian Application No. 14-026502; 8 pages.
Non-Patent Literature Document—"Aqueous Coating—Aquacoat ECD," FMC Biopolymer; 12 pages.
Non-Patent Literature document—"Brief Communication," dated Feb. 10, 2011, issued by the European Patent Office, corresponding to European Application No. 06778240.9 (European Patent No. 1 931 316); 1 page.
Non-Patent Literature document—"Vollmacht Authorisation Pouvoir," (German document—Power of Representation before the EPO for European Patent No. 1 931 316, dated Sep. 13, 2011; 3 total pages.
Non-Patent Literature document—"Claims—First Auxillary Request" and "Claims—Second Auxillary Request," dated Sep. 2011, corresponding to Opposition Proceedings of European Patent. No. 1 931 316; 12 total pages.
Non-Patent Literature document—"Brief Communication—Main Request,", dated Jun. 17, 2011, corresponding to European Patent No. 1 931 316; 8 total pages.
Non-Patent Literature document—"Notice of Opposition to a European Patent," dated Nov. 15, 2010, corresponding to European Patent No. 1 931 316; 5 pages.
Non-Patent Literature document—"Decision to grant a European patent pursuant to Article 97(1) EPC," corresponding to European Patent No. 1 931 316, dated Jan. 21, 2010; 2 pages.
Non-Patent Literature document—"A2PAMPHLET," related to WO 2007/020259 (PCT/EP2006/065311), printed on May 19, 2008, 29 total pages.
Non-Patnet Literature document—"Claims (EP 06 778 240)" printed Sep. 25, 2008; 12 total pages.
Naftifine HCI—MSDS—Material Safety Data Sheet, created Jun. 23, 2004; http://pharmacycode.com/msds/Naftifine_HCI; 4 pages.
Australian Patent Examination Report No. 2, dated Feb. 25, 2016, corresponding to Australian Application No. 2014203364; 5 pages.
Egyptian Office Action (No English translation available), dated Mar. 20, 2016, corresponding to Egyptian Application No. PCT 1257/2009; 5 pages.
Japanese Office Action (with English translation), dated Mar. 1, 2016, corresponding to Japanese Application No. 2014-524476; 5 total pages.

Chinese Office Action (No English translation available), dated Feb. 15, 2016, corresponding to Chinese Application No. 201180055719. X; 14 pages.
"Polymer Science in Pharmaceutics", Junmin Zheng, China Medical Science Press, pp. 113-114, Jan. 31, 2009)—Article Unavailable.
Mexican Office Action (No English translation available), corresponding to Mexican Application No. MX/a/2013/003627, dated Mar. 10, 2016; 2 pages.
International Preliminary Report on Patentability and Written Opinion of the International Searching Authority, dated Feb. 9, 2016, corresponding to International Application No. PCT/US2014/049569; 7 total pages.
Korean Notice of Final Rejection (with English translation), dated Dec. 28, 2015, corresponding to Korean Application No. 10-2015-7004820; 8 total pages.
Canadian Office Action dated Mar. 16, 2016, corresponding to Canadian Application No. 2,677,989; 4 pages.
Malaysian Office Action dated Mar. 31, 2016, corresponding to Malaysian Application No. PI 2012001215; 3 pages.
Israeli Office Action (No English translation available), dated Apr. 3, 2016, corresponding to Israeli Application No. 218656; 2 pages.
Sankalia M.G. et al., "Papain Entrapment in Alginate Beads for Stability Improvement and Site-Specific Delivery: Physicochemical Characterization and Factorial Optimization Using Neural Network Modeling," AAPS PharmSciTech., 2005; vol. 6, No. 2, Article 31; pp. E209-E222.
Scheich C. et al., "An Automated In Vitro Protein Folding Screen Applied to a Human Dynactin Subunit," Protein Science, 2004, vol. 13; pp. 370-380.
Miller D.A. et al., "Evaluation of the USP Dissolution Test Method A for Enteric-Coated Articles by Planar Laser-Induced Fluorescence," International Journal of Pharmaceuticals, 2007, vol. 330; pp. 61-72.
Ramos et al., "Time-Resolved Fluorescence Allows Selective Monitoring of Trp30 Environmental Changes in the Seven-Trp-Containing Human Pancreatic Lipase," Biochemistry 2003, vol. 42; pp. 12488-12496.
International Search Report, Written Opinion and International Preliminary Report on Patentability based on International Application No. PCT/IB2008/000770, dated Jun. 3, 2009; 13 Pages.
Krishnamurty et al., "Delayed release pancrelipase for treatment of pancreatic exocrine insufficiency associated with chronic pancreatitis," Therapeutics and Clinical Risk Management, (2009:5) pp. 507-520.
Drugs@FDA Glossary of Terms, printed Nov. 20, 2009; http://www.fda.gov/Drugs/InformationonDrugs/ucm079436.htm; 7 pages.
Guidance for Industry #191, Changes to Approved NADAs—New NADAs vs. Category II Supplemental NADAs, Final Guidance, U.S. Department of Health and Human Services, Food and Drug Administration, Center for Veterinary Medicine, Released Nov. 19, 2009: 25 pages.
Singapore Written Opinion, corresponding to Singapore Patent Application No. 200905385-1, issued by the Austrian Patent Office dated Dec. 16, 2010; 6 pages.
International Search Report, Written Opinion and International Preliminary Report on Patentability based on International Application No. PCT/IB2008/000770, dated Jun. 3, 2009; (13 Pages).
Hageman, "The Role of Moisture in Protein Stability," Drug Development and Industrial Pharmacy, vol. 14, No. 14, (1988); pp. 2047-2070.
Maul and Schmidt, "Influence of different-shaped pigments on bisacodyl release from Eudragit L 30 D," International Journal of Pharmacetuics, vol. 118, No. 1, May 1, 1995; pp. 103-112.
Maul and Schmidt, "Influence of different-shaped pigments and plasticizers on theophylline release from Eudragit RS30D and Aquacoat ECD30 coated pellets," S.T.P. Pharma Sciences, vol. 7, No. 6, pp. 498-506.
Felton and McGinity, "Influence of Insoluble Excipients on Film Coating Systems," Drug Development and Industrial Pharmacy, vol. 28, No. 3; pp. 225-243.

(56) References Cited

OTHER PUBLICATIONS

Parker et al., "Effects of Solids-Loading on Moisture Permeability Coefficients of Free Films," Journal of Pharmaceutical Sciences, vol. 63, No. 1 (Jan. 1974); pp. 119-125.
Thoma and Bechtold, "Influence of aqueous coatings on the stability of enteric coated pellets and tablets," European Journal of Pharmaceutics and Biopharmaceutics, vol. 47, (1999), pp. 39-50.
Nordmark pancreatin brochure, Products all over the World, (publication year unknown); 7 pages.
Australian First Examination Report, dated Mar. 23, 2012, corresponding to Australian Patent Application No. 2008218595; 2 pages.
English Translation of Second Chinese Office Action, dated Apr. 12, 2012, corresponding to Chinese Patent Application No. 200880012762.6; 5 pages.
European Communication, dated Jan. 3, 2012, corresponding to European Patent Application No. 08719392.6; 7 pages.
European Communication, dated Aug. 1, 2012, corresponding to European Patent Application No. 08719392.6; 7 pages.
New Zealand First Examination Report, dated Aug. 26, 2010, corresponding to New Zealand Patent Application No. 579047; 3 pages.
New Zealand Second Examination Report, dated Dec. 15, 2011, corresponding to New Zealand Patent Application No. 579047; 2 pages.
New Zealand First Examination Report, dated Feb. 29, 2012, corresponding to New Zealand Patent Application No. 598477; 1 page.
Singapore Second Written Opinion, dated Nov. 22, 2011, corresponding to Singapore Patent Application No. 200905385-1; 6 pages.
U.S. Office Action, dated Mar. 20, 2012, corresponding to U.S. Appl. No. 12/034,480; 7 pages.
U.S. Office Action, dated Oct. 14, 2011, corresponding to U.S. Appl. No. 12/034,480; 15 pages.Office Action for U.S. Appl. No. 12/034,480, dated Oct. 14, 2011, 15 pages.
U.S. Office Action, dated Mar. 19, 2012, corresponding to U.S. Appl. No. 12/034,488; 8 pages.
U.S. Office Action, dated Oct. 25, 2011, corresponding to U.S. Appl. No. 12/034,488; 14 pages.
U.S. Office Action, dated Jan. 4, 2012, corresponding to U.S. Appl. No. 12/034,491; 7 pages.
U.S. Office Action, dated Jun. 23, 2011, corresponding to U.S. Appl. No. 12/034,491; 7 pages.
U.S. Office Action, dated Jun. 26, 2012, corresponding to U.S. Appl. No. 13/019,844; 15 pages.
U.S. Office Action, dated May 24, 2012, corresponding to U.S. Appl. No. 13/019,856; 9 pages.
U.S. Office Action, dated May 23 2012, corresponding to U.S. Appl. No. 13/019,860; 5 pages.
U.S. Office Action, dated Jul. 2, 2012, corresponding to U.S. Appl. No. 12/832,596; 11 pages.
International Search Report and Written Opinion, dated Oct. 22, 2012, corresponding to International Application No. PCT/US2010/049203; 6 pages.
Canadian Office Action, dated May 6, 2014, corresponding to Canadian Application No. 2,677,989, 2 pages.
Colombian Office Action (with No English translation), dated May 26, 2014, corresponding to Colombian Application No. 09.101.677, 4 pages.
Costa Rica Preliminary Technical Report—1st Phase, corresponding to Costa Rica Application No. 11031, dated Jun. 12, 2014; 11 total pages.
European Communication dated Apr. 8, 2014, corresponding to European Application No. 08 719 392.6, 6 pages.
Indian Office Action, dated Oct. 17, 2014, corresponding to Indian Application No. 5854/DELNP/2009; 4 pages.
Japanese Decision of Rejection and Decision of Dismissal of Amendment (with English translations), dated Aug. 25, 2014, corresponding to Japanese Application No. 2009-549868; 9 total pages.
Singapore Search Report, dated Apr. 7, 2014 and Singapore Written Opinion, dated Apr. 28, 2014, corresponding to Singapore Application No. 2012091583; 11 total pages.
Japanese Office Action (with English translation), dated Jan. 19, 2015, corresponding to Japanese Application No. 2013-265143, 11 total pages.
Taiwanese Office Action and Search Report (with English translation, dated Oct. 3, 2014, corresponding to Taiwanese Application No. 102138934; 10 total pages.
Colombian Office Action (with No English translation), dated Sep. 23, 2014, corresponding to Colombian Application No. 14.026.502, 4 pages.
The Decision of the Enlarged Board of Appeal, dated Nov. 22, 2013, 18 pages.
The Minutes of the Oral Proceedings of Nov. 22, 2013, 6 pages.
Communication from the Enlarged Board of Appeal pursuant to Articles 13 and 14(2) RPEBA, dated Sep. 17, 2013; 6 pages.
Letter from Botti & Ferrari regarding a Petition for Review of Decision T0977/09-3.3.02, European Patent No. 1 335 706 in the name of Aptalis Pharma S.r.l., dated May 15, 2013; 12 pages.
Termination of Opposition Proceedings of Patent No. 01994654.0-1456 / 1335706 with Revocation of the Patent, dated Mar. 14, 2013; 2 pages.
Decision dated Nov. 30, 2012; 28 pages.
The Minutes of the Oral Proceedings of Nov. 30, 2012; 18 pages.
International Search Report, International Preliminary Report on Patentability and Written Opinion of the International Searching Authority, corresponding to International Application No. PCT/IB2012/054050, dated Nov. 14, 2012; 11 total pages.
Eurasian Office Action (with English translation), dated May 30, 2016, corresponding to Eurasian Application No. 201590835/28; 4 total pages.
Eurasian Office Action (with English translation), dated May 30, 2016, corresponding to Eurasian Application No. 201590836/28; 4 total pages.
Eurasian Office Action (with English translation), dated Jun. 8 2016, corresponding to Eurasian Application No. 201390409/28; 4 total pages.
Chinese Office Action (No English language translation available), dated Jul. 5, 2016, corresponding to Japanese Application No. 201180055719.X; 14 pages.
Taiwanese Office Action with English tranlsation of Search Report, dated May 13, 2016, corresponding to Taiwaense Application No. 099131496; 5 total pages.
Australian Patent Examination Report No. 3, dated Jun. 28, 2016, corresponding to Australian Application No. 2014203364; 3 pages.
English translation of Chinese Third Office Action, dated Jun. 28, 2016, corresponding to Chinese Application No. 201410059861.7; 4 pages.
Korean Office Action (with English translation) dated May 16, 2016, corresponding to Korean Application No. 10-2015-7004820; 10 total pages.
Australian Patent Examination Report No. 1, dated Sep. 21, 2016, corresponding to Australian Application No. 2015243026; 3 pages.
Chilean Office Action (No English translation available), dated Aug. 22, 2016, corresponding to Chilean Patent Application No. 2014-00315; 8 pages.
English translation of Israeli Office Action dated Aug. 30, 2016, corresponding to Israeli Application No. 243627; 2 pages.
Takanami et al., "Enzyme-assisted Purification of Two Phloem-limited Plant Viruses: Tobacco Necrotic Dwarf and Potato Leafroll", J. gen. Virol., vol. 44, (1979); pp. 153-159.
Tolin et al., "Purification and Serology of Peanut Mottle Virus", The American Phytopathological Society, vol. 73, No. 6, 1983; pp. 899-903.
Casas et al., "Detection of enterovirus and hepatitis A virus RNA in mussels (*Mytilus* spp.) by reverse transcriptase-polymerase chain reaction", Journal of Applied Microbiology, vol. 90, 2001; pp. 89-95.

(56) References Cited

OTHER PUBLICATIONS

Lewis et al., "Polyethylene Glycol Precipitation for Recovery of Pathogenic Viruses, Including Hepatitis A Virus and Human Rotavirus, from Oyster, Water, and Sediment Samples", Applied and Environmental Microbiology, vol. 54, No. 8, Aug. 1988; pp. 1983-1988.
Schwab et al., "Concentration and Purification of Beef Extract Mock Eluates from Water Samples for hte Detection of Enteroviruses, Hepatitis A Virus, and Norwalk Virus by Reverse Transcription-PCR", Applied and Environmental Microbiology, vol. 61, No. 2, Feb. 1995; pp. 531-537.
A. Aloulou, et al., "In Vitro Comparative Study of Three Pancreatic Enzyme Preparations: Dissolution Profiles, Active Enzyme Release and Acid Stability", Alimentary Pharmacology & Therapeutics, vol. 27, No. 3; Oct. 29, 2007; pp. 283-292.
A. C. Mehta, "Review of analytical methods used in the dissolution testing of pharmaceuticals", Analytical Proceedings Induding Analytical Communications, vol. 31, No. 8, Jan. 1, 1994; pp. 245-248.
Alexey Khrenov: "USP Pancrelipase update", Jul. 1, 2009 and Alexey Khrenov: "USP Enzyme WOrkshop: Pancrelipase Update", Jul. 1, 2009.
"Dissolution Toolkit—Procedures for Mechanical Calibration and Performance Verification Test", USP(U.S> Pharmacopeia), Mar. 22, 2010.
New Zealand First Examination Report corresponding to New Zealand Application No. 620329, dated Oct. 16, 2014; 2 pages.
Colombian Office Action with English translation, dated Oct. 29, 2014, corresponding to Colombian Application No. 14-33910; 17 total pages including English translation.
Coutlee, et al., "Comparison of Colorimetric, Fluorescent, and Enzymatic Amplification Substrate Systems in an Enzyme Immunoassay for Detection of DNA-RNA Hybrids", Journal of Clinical Microbiology, vol. 27, No. 5, May 1989, pp. 1002-1007.
Fuhrmann, et al., "In Vivo Fluorescence Imaging of Exogenous Enzyme Activity in the Gastrointestinal Tract", Proceedings of the National Academy of Sciences of the USA, vol. 108, No. 22, May 2011; pp. 9032-9037.
Zang, et al., "Quantitative Fluorescence Correlation Spectroscopy Reveals a 1000-Fold Increase in Lifetime of Protein Functionality", Biophysical Journal, vol. 95, Oct. 2008; pp. 3439-3446.
(Guidance for Industry) "SUPAC-MR: Modified Release Solid Oral Dosage Forms Scale-Up and Postapproval Changes: Chemistry, Manufacturing and Controls; In Vitro Dissolution Testing and In Vivo Bioequivalence Documentation" Center for Drug Evaluation and Research (CDER), Sep. 1997.
Australian Patent Examination Report No. 1, dated May 20, 2014, corresponding to Australian Application No. 2012293325; 3 pages.
Chinese Office Action dated Dec. 2, 2014 (with No English translation), corresponding to Chinese Application No. 201280040203.2; 6 pages.
Colombian Office Action (English Summary), corresponding to Colombian Application No. 13-66300; 2 pages.
Eurasian Office Action dated Jun. 30, 2014 (with English translation), corresponding to Eurasian Application No. 201390409; 5 total pages.
Handbook of Pharmaceutical Excipients, Fifth Edition, Edited by Raymond C. Rowe, et al. 4 pages.Rowe, et al., Handbook of Pharmaceutical Excipients, 4 pages.
Austrailian Patent Examination Report No. 1, dated Oct. 14, 2014, corresponding to Austrailian Application No. 2011309763; 3 pages.
European Search Report corresponding to European Application No. 14176579.2, dated Nov. 28, 2014, 4 pages.
English translation of Colombian Office Action, corresponding to Colombian Application No. 13-066300; 7 pages.
Chinese Office Action (No English translation), dated Jan. 6, 2015, corresponding to Chinese Application No. 201180055719.X; 18 pages.
Masaki Hasegawa, Direct Compression Microcrystalline Cellulose Grade 12 versus Classic Grade 102, Pharmaceutical Technology, pp. 50-60, May 2002.

Australian Patent Examination Report No. 1 corresponding to Australian Application No. 2010295494, dated Apr. 28, 2014; 3 pages.
Extended European Search Report, corresponding to European Application No. 10817867.4, dated May 26, 2014; 6 pages.
Symersky T., et al. "An Explorative Study on the Effect of Enzyme Supplementation in Patients Recovered From Acute Pancreatitis", Gastroenterology 2004; 126 (4 suppl 2): A85, Abstract 653.
Taiwanese Office Action dated Jul. 21, 2014; 6 pages.
Tawianese Search Report corresponding to Taiwanese Application No. 099131496, dated Jul. 16, 2014, 1 page.
Russian Office Action (with English Translation) corresponding to Russian Application No. 2012113253, dated Jul. 7, 2014; 8 total pages.
Colombian Office Action issued by the Colombian Patent Office dated Aug. 22, 2014 (with no English translation), corresponding to Colombian Application No. 12-50658, 9 pages.
Chilean Office Action (without English Translation) dated Oct. 8, 2014, corresponding to Chilean Patent Application No. 00658-2012; 8 pages.
Japanese Notice of Rejection dated Sep. 24, 2014 (with English Translation), corresponding to Japanese Application No. 2012-529909; 6 pages.
Chinese Office Action (with No English translation), corresponding to Chinese Application No. 201080041366.3, dated Nov. 24, 2014; 3 pages.
Russian Office Action (with English translation), corresponding to Russian Application No. 2012113253, dated Nov. 25, 2014; 11 total pages.
Taiwanese Office Action (with English translation), corresponding to Taiwanese Application No. 099131496, dated Nov. 26, 2014; 10 total pages.
Pakastan Examination Report, corresponding to Pakistan Application No. 804/2010; 1 page.
English translation of Israeli Office Action, corresponding to Israeli Application No. 218656, dated Nov. 23, 2014; 2 pages.
Eurasian Office Action (with English Translation) dated Jan. 30, 2015, corresponding to Eurasian Application No. 201390409/28; 4 total pages.
International Search Report, and Written Opinion of the International Searching Authority, corresponding to International Application No. PCT/IB2011/002419, dated Feb. 6, 2012; 8 total pages.
Korean Office Action (with English translation), dated Nov. 24, 2014, corresponding to Korean Application No. 10-2009-7019590; 6 total pages.
Non-patent literature cited during the Appeal Procedure (universitatbonn) (D22), dated Jun. 17, 2010; 6 pages.
Letter dated Aug. 5, 2010, relating to the Appeal Procedure (Eisenfuhr Speiser); 10 pages.
Letter from Prof. Dr. Klaus-Jurgen Steffens, Rheinische Friedrich-Wilhelms-Universitat Bonn to the European Patent Office, Munich, dated Jun. 17, 2010, "Expert Opinion for Presentation at the European Patent Office"; 6 pages.
ScienceLab.com, Chemicals & Laboratory Equipment, Polyethylene Glycol 400 MSDS, Material Safety Data Sheet (D12), dated Oct. 10, 2005; 6 pages.
Kahn, et al., Bovine Pancreatic Lipase1. II. Stability and Effect of Activators and Inhibitors, Journal of Dairy Science, vol. 59, No. 5, pp. 840-846.
Worthington Biochemical Corporation, Lipase—Worthington Enzyme Manual, Triacylglycerol acylhydrolase, (D14); www.worthington-biochem.com; Jun. 24, 2009; 2 pages.
Caelo, Macrogol 4000 Pulver, Sicherheitsdatenblatt, Seitel, von 3, (D15) dated Aug. 4, 2008; 3 pages.
Answers.com, Stir. Difinition, Synonyms of the word "Stir" from Answers.com, (D16), Jun. 24, 2009; 9 pages.
Office Action issued by the U.S. Patent and Trademark Office dated Apr. 1, 2009, corresponding to U.S. Appl. No. 10/416,702, 24 pages.
Final Office Action issued by the U.S. Patent and Trademark Office dated Jul. 14, 2008, corresponding to U.S. Appl. No. 10/416,702, 12 pages.
Fuhrmann, Vorlesungen uber, Technische Mykologie, Verlag Gustav Fisher 1913, 80; (D19); 4 pages.

(56) References Cited

OTHER PUBLICATIONS

Mesh to Micron Conversion Chart—Fluideng.com, Copyright 2002—Property of TM Industrial Supply, Inc.; (D20); http://www.fluideng.com/FE/meshmicron.html; 1 page.

* cited by examiner

MICROSPHERES OF PANCREATIC ENZYMES WITH HIGH STABILITY AND PRODUCTION METHOD THEREOF

CROSS REFERENCE TO RELATED APPLICATIONS

This application is a continuation of U.S. patent application Ser. No. 10/416,702, filed May 14, 2003, which is a National Stage Entry of PCT/EP01/13115, filed Nov. 13, 2001 and claims the benefit of and priority to Italian Patent Application No. MI2000A002456, filed Nov. 15, 2000, the entire contents of each of the applications are hereby incorporated by reference herein in their entirety.

FIELD OF THE INVENTION

The present invention refers to the production of microparticles for pharmaceutical use. Microspheres including pancreatic enzymes in stabilized form are described, with high bio-availability and high enzymatic activity. It is moreover described the production process of said microspheres through a high-energy granulation and spheronisation process, without the presence of solvents.

PRIOR ART

A reduced exogenous production of enzymes by the pancreatic gland can be due to different pathologic conditions. The unsuccessful or insufficient production of digestive enzymes in particular is due to the mucoviscidosis (cystic fibrosis), to obstructions of the common bile duct, to pancreatic carcinoma and to pancreas inflammatory states (chronic pancreatitis). As a consequence the persons affected with these pathologies become unable to digest the foods by decomposing them into molecules absorbable by the gastrointestinal tract.

The disease brings to loss of weight and can have deadly outcome. The therapy consists of substitute oral administration of pancreatic enzymes of animal origin (here called "pancreatin" for the sake of brevity). The pancreatin is formed for the most part by lipase, amylase and protease; mainly the lipase catalyses the hydrolysis of the fats into fatty acids and glycerol, the amylase metabolizes the starch into dextrins and sugars and the protease decomposes the proteins into peptides and amino acids (G. J. Peschke, Pancreatic enzymes (Pancreatin), in Topics in pharmaceutical sciences, D. D. Breimer, D. J. A. Crommelin, K. K. Midha, Fédération Internationale Pharmaceutique (FIP), The Hague, 1989).

The pancreatin is extracted, preferably but not only, from the pig pancreas.

The pharmaceutical most suitable and effective form for pancreatin is that of spheres or pellets or minitablets. In case of oral administration, these formulations are provided with gastroresistant coatings: this is necessary by the fact that the pancreatic enzymes are inactivated by the acid pH of the stomach and must be delivered just when in contact with the duodenal pH.

The administration of small-sized multiparticles forms is particularly important to ensure a proper distribution of the enzymes in the food during the gastric transit and a remarkable delivery rate when the microspheres reach the duodenal pH. To improve the food digestion, it is particularly important that the microsphere are small sized, so that the enzymes are delivered onto a wide surface area and have a fast gastric transit. To this purpose Meyer has demonstrated that spheres of 1 mm passed through the stomach with times significantly shorter than spheres of 2 or 3 mm diameter (J. H. Meyer, J. Elashoff, V. Porter-Fink, J. Dressman, G. L. Amidon, Gastroenterology, 94, 1315, 1988).

Pancreatin is an enzyme with particular stability problems: it is in fact been noticed its inactivation, partial or total, in case of long exposure to water environment or heating at high temperature, or for simple storage at high temperature (G. J. Pescke, Pancreatic Enzymes (Pancreatin) ch. 10, p. 133). The most unstable among the pancreatic enzymes proves to be the lipase, which is also the most important enzyme in the substitute therapies. In tests made by the Applicant the pancreatin, preserved for 7 days at 40° C. at 75% relative humidity, loses 45% to 60% of enzymatic activity (lipase).

The pancreatin lability problems have influenced all the production processes of microparticles of said enzyme, reducing the range of the micronisation processes applicable to this product.

M. Buu describes (patent TW-A-310277) the preparation of an extrudate product obtained through water granulation, desiccation, re-granulation, extrusion and following selection. JP-A-08109126 claims a production method based on the application in fluid bed of pancreatin powder on sugar spheres through the simultaneous atomisation of a water solution containing a ligant (hydroxypropylcellulose). An analogous method is described in EP-A-277741, where it is described the use of LHPC (low viscosity hydroxypropylcellulose) in water solution to apply powdered pancreatin on inert nuclei (Nonpareil seeds). All these methods involve the contact of pancreatin with water and/or other solvents in dynamic conditions of particles mixing; as also highlighted in the experimental part of the present application, the wet granulation leads to a partial denaturation of pancreatin, with the formation of granules less active than the native enzyme.

An example of preparation of pancreatin pellets without use of solvents is described by Faassen and Vromans in WO-A-9638169: pancreatin is compressed by means of a roll compactor and then shelled to obtain irregularly-shaped pellets. Boedecker et al. have obtained regularly-shaped pellets through extrusion and following spheronisation: in their EP-A-583726 is described the production of pellets with sizes included between 0.7 and 1.4 mm. An extrusion process is used also in the patent JP-A-04187085, to obtain pellets with sizes 1.5 to 3 mm; as extrusion solvent is used water or a mixture of water and ethyl alcohol. Atzl et al. (WO-A-9107948) use a process similar to wet granulation to obtain spherical particles with sizes 0.3 to 4 mm. In DE-A-A3422619 minitablets are obtained with diameter of 1-2.5 mm and height 1-2.5 mm through compression with suitably modified punches. In DE-A-2923279, assigned to Fischer et al., pancreatin is extruded in presence of isopropyl alcohol or acetone, spheronized and finally desiccated.

The above mentioned extrusion processes give irregular surface particles which require further size homogenization processes, with consequent longer production time and greater enzyme inactivation risk. This goes to the detriment of the enzyme stability and involves high industrial costs; moreover, as proved in the experimental part, the extrusion processes in presence of solvent, presents serious problems of loss of enzymatic activity. In the light of the prior art, it lacks an efficient process, having an industrial low cost, giving a very fine pellet size without causing denaturation and loss of enzymatic activity; moreover are not yet available pancreatin microspheres with reduced size and high enzymatic activity.

SUMMARY

The present invention refers to new microspheres including pancreatic enzymes, pharmaceutical compositions containing them, and a process to obtain them. The process here described does not involve the use of solvents and proves to be remarkably shorter and efficient than the prior art methods. The obtained microspheres, including one or more pancreatic enzymes, one or more hydrophilic low-melting polymers and eventual excipients, have a high enzymatic activity, bio-availability and stability.

FIGURES DESCRIPTION

Figure 1B:
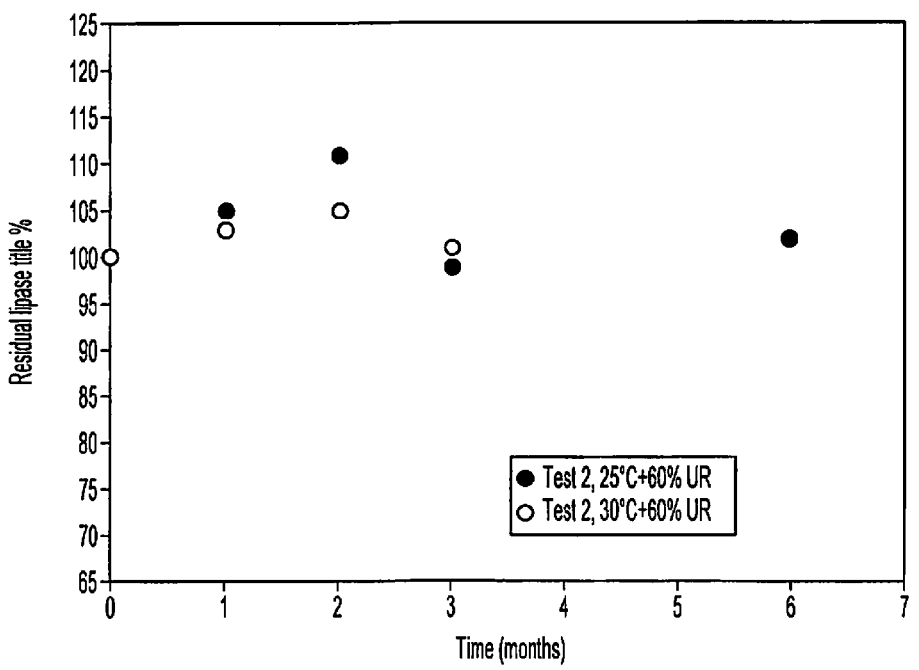

FIGS. 1A and 1B: Course of the enzymatic titer (lipase) of microsphere produced according to the present invention, during 6 months period.

DETAILED DESCRIPTION OF THE INVENTION

Object of the present invention is a process allowing to obtain microspheres of pancreatic enzymes having extremely reduced sizes and a high and stable enzymatic activity.

The process is characterized in that a solid mixture including one or more pancreatic enzymes, one or more hydrophilic low-melting polymers and eventual excipients, is heated at a temperature equal or higher than the melting temperature of said hydrophilic low-melting polymer, under stirring.

The components of the mixture to be used in the process are described in detail as follows.

With "pancreatic enzymes" is meant any one of the enzymes included in the pancreatic secretion, such as amylase, lipase, protease, or their mixture in any proportion, or any extract of pancreatic origin having enzymatic activity, such as pancreatin.

Said enzymes can be indifferently obtained through extractive way from the pancreas, or produced artificially, for example through synthetic or recombinant way; in the present process they are preferably used in form of powder.

The hydrophilic low-melting polymer has melting point between 20° C. and 90° C., preferably between 30° C. and 70° C. Examples of hydrophilic low-melting polymers are: polyethylene glycol (Lutrol E®, Sentry® Carbonwax®), polyoxyethylene (Sentry® Polyox® WSR), copolymers of polyoxyethylene-polyoxypropylene (Lutrol F®).

The spheronisation mixture can include as well other excipients normally used in the pharmaceutical art, for example lubricants, glidants, coloring agents, diluents. Among these last ones it can be mentioned lactose (anhydrous or hydrate), microcrystalline cellulose (Avicel®, Emcocel®), calcium phosphate (Di Cafos®). In general, all the excipients which could improve or make more efficient the spheronisation can be added to the composition The composition of the mixture subjected to the process object of the invention includes: pancreatic enzyme/s, in weight rate between 40% and 99%, preferably between 60% and 85%, and hydrophilic polymer/s, between 1% and 60%, preferably between 15% and 40%.

The ratio between enzyme and hydrophilic low-melting polymer in the starting mixture is preferably between 4:1 and 1:1.

In the process object of the invention, the above-described mixture is aggregated in micropellets and the micropellets are simultaneously subjected to a spheronisation process which regularise their surface. The process in question includes, in particular, the following stages:

a: loading of a suitable reactor with said solid mixture or with its single components in solid state;
b: stirring of the mixture under high-energy condition and heating of the mixture at
a temperature equal or higher than the melting temperature of said hydrophilic polymer;
c: cooling of the mixture under stirring condition;
d: recovery of the solidified microspheres.

In case the mixture includes more hydrophilic low-melting polymers, the mixture is heated at a temperature corresponding or higher than the melting temperature of the polymer with the highest melting point.

A fundamental feature to obtain the microspheres with the here described properties is to avoid the direct adding of any liquid to the solid mass. The process is then carried out in total absence of solvents, both watery or organic, and avoiding any adding to the solid mass of polymers in melted state; it is then critical that all the mixture components are introduced into the reactor in the solid state before any heating is started.

The process is advantageously performed in a granulator-mixer or fluid bed. Devices preferred for the performing of the process are the high-energy granulator-mixers, such as for example Zanchetta Roto, Diosna P, Niro Pellmix, Henschel, Robot Coupe RSI, Glatt VG, or the fluid beds provided with rotating disc such as for example the Glatt ones with Rotor insertion, the Aeromatic ones provided with rotating disc, the ICO PaG ones with insertion "tangential spray" and the Victor one series FL "rotary disc".

All these devices have in common that the mixture is subjected to a high-energy mixing action and is simultaneously heated at a temperature higher or equal to the melting one of the used hydrophilic polymer.

The stirring and heating action is performed for a total time (for instance 30 minutes-75 minutes) sufficient to obtain the desired spheronisation degree. The temperature is then lowered to allow the microspheres to solidify; the mixing goes on, eventually with less energy, during the solidification stage (for instance for 10 minutes-50 minutes); the process ends with the interruption of the mixing and the recovery of the microspheres. The whole process normally takes between 15 minutes and 150 minutes, preferably 50 minutes and 100 minutes.

The microspheres can be sieved through a vibrating sieve to reject eventual particles out of the required size standards.

The so obtained microspheres, in particular the ones destined to the oral administration, are advantageously provided with a gastroresistant coating, (preferably non soluble at pH lower than 5.5), such to ensure the delivery of the active principle just when the duodenum is reached, this way protecting it from the gastric pH; the application of said coating polymers is performed through spraying according to the prior art, in a fluid bed or in a spraying pan: coating is easy because of the spherical and regular surface of the microspheres. Examples of gastroresistant polymers which can be applied are: hydroxypropylmethylcellulose phthalate (for instance HP-50 or HP-55), hydroxypropylmethylcellulose acetate succinate (Aqoat®), acrylates (for instance Eudragit® L30D) polyvinylacetophthalate (Sureteric®). To improve the applicability and the stability of the polymeric membranes formed by these polymers it can be added, mixed to the same coating, plasticizing agents such as for instance, triethylcitrate or dibutylphthalate. Moreover the gliding agents like the talc are helpful to reduce the adhesion among the pellets during the coating process.

The hydrophily of the above mentioned hydrophilic low-melting polymers allow the microspheres of the invention to quickly get the enzymes bio-available in the duo-denal environment, once the gastroresistant coating is dissolved.

A further object of the invention are microspheres of pancreatic enzymes with high bio-availability, produced according to the above described process.

The present process allows in fact to obtain new microspheres of pancreatic enzymes, having the following features: (a) reduced size, with diameter between 10 μm and 1500 μm, preferably between 100 μm and 800 μm, thus with a high bio-availability of the enzyme once administered; (b) high enzyme titer; with high enzymatic titer is meant an enzymatic titer of the microsphere (measured in unit FIP/mg) equal to or higher than 90%, preferably equal to or higher than 95%, than the titer of the solid mixture (enzyme, hydrophilic polymer and excipients in their initial quantities) from which they were produced; said mixture is in the following indicated as "physical mixture of their components". In other words, the activity of the pancreatic enzyme contained in the present microspheres is ≥90%, preferably ≥95% of the activity of the native, untreated enzyme.

In case the microspheres include more than one pancreatic enzyme, the above mentioned enzymatic titer is to be determined with reference to the activity of the most thermolabile among them; for instance, in the case of the pancreatin (which includes lipase, amylase and protease), the enzyme whose titer is measured is the lipase.

The microspheres according to the present invention have a high surface regularity and a prolonged stability of the enzymatic titer in time.

The microspheres obtained according the present invention include: one or more pancreatic enzymes, in weight ratio between 40% and 99%, preferably between 60% and 85%; one or more hydrophilic polymers, in quantity from 1% to 60%, preferably between 15% and 40%, and excipients pharmaceutically acceptable.

A further object of the invention are pharmaceutical compositions including the above described microspheres (eventually coated with coating polymers) and other excipients suitable for the pharmaceutical use, for example lubricants, gliding agents, coloring agents, diluents, etc. Said compositions can be formulated in forms suitable for the human or animal administration, for instance powders or pellets in sachets to dilute into water when used, suspensions, capsules of hard or soft gelatine, tablets or microtablets.

The present invention offers several advantages: the direct spheronisation process is quick and inexpensive, since it is not necessary to use organic solvents, expensive and potentially dangerous if wasted in the environment, nor water, which requires long desiccation times and could inactivate the enzymes. Contrary to all expectations, this process can be efficiently performed even at temperatures higher than the ones of said enzymes denaturation, without reducing the activity in the least. The so produced microspheres have a very reduced diameter, lower than 700 μm on average, thus allowing a high bio-availability. The microspheres' regular surface allows to obtain pharmaceutical coated forms using a smaller quantity of coating polymers than irregular shaped pellets: this allows to reduce the quantity of coating agent and the time required for the coating, so reducing the process costs and the enzyme inactivation risks. As highlighted in the experimental part, the microspheres have an enzymatic titer substantially unchanged as the native enzyme and a high activity persistence in storage condition, so allowing the production of pharmaceutical compositions of pancreatic enzymes with high activity and stability.

The present invention is now described through the following not limitative examples.

EXPERIMENTAL PART

The production techniques of microspheres including pancreatic enzymes used as comparison with the present invention are: application of pancreatin on inert nucleus seed (ex. 1); extrusion and spheronisation (ex. 2). The process according to the present invention (direct spheronisation) is performed in a fluid bed with rotating disc (ex. 3), or with high-energy granulator-mixer (ex. 4). The enzymatic activity is measured as lipasic activity: this enzyme has been chosen as reference since it is the most labile among the pancreatic enzymes. The activity is determined according to analytical assays of biological type described in the European and American Pharmacopoeia and are expressed in Unit/mg (Unit FIP or Unit USP according to the used assay). According to the European Pharmacopoeia 1 mg of pancreatin has to contain not less than 1 U-FIP of proteolitic activity, not less than 15 U-FIP of lipolitic activity and not less than 12 U-FIP of amilolitic activity.

Example 1 (Reference)

Preparation of Pancreatin Pellets Through Powder Application on Inert Nuclei

In the basket of a fluid bed of the type Glatt GPCG-1 provided with rotor insertion (rotating disc) are placed 798.0 g of neutral pellets (type "non-pareil seeds", formed by saccharose and maize starch) having sizes included between 250 and 350 μm The pellets are heated to 23° C. by blowing warm air at 28° C. The entering air speed is 1 m/sec for the process whole time. Separately the powdered pancreatin is mixed with the 2.0% by weight of colloidal silica (Aerosil® V200) to improve its flow-ability. The entering air temperature in the fluid bed is increased to 54° C. so that the pellets temperature is about 27-28° C. and 490.0 g of said mixture are applied through proportioning device Heton Feeder at a rate of 26 g/min, while simultaneously demineralized water is sprayed through a nozzle with a 0.8 mm hole and a flow rate of about 5-6 g/min. The filtering hoses are shaken for 5 seconds any 12 sec at the beginning of the process. After 25 minutes application it is necessary to shake the hoses for 5 sec any 6 sec. The pellets are desiccated by blowing air at 50° C., so to remove traces of residual water, and finally cooled by 30° C. air for 10 minutes. The total time of the process is 120 minutes. This technique involves long process times since large amounts of active principle are brought into the filtering hoses by the air stream; the size of the microspheres is difficult to control. The theoretical titer of the pellets (lipase), calculated by the composition, is 18.27 U-USP/mg. The obtained lipase titer is, on the contrary, 8.39 U-USP/mg. This technique involves a loss in the enzymatic activity equal to 54%.

Example 2 (Reference)

Preparation of Pancreatin Pellets Through Extrusion-spheronisation 660.0 g of pancreatin, 2465.1 g of Avicel® PH101 (microcrystalline cellulose), 165.0 g of Kollidon® K30 (polyvinylpyrrolidone) and 9.9 g of Syloid®244 (colloidal silica) are mixed in an 18 liters mixing cube at 18 rpm for 15 minutes. The mixture is fed through a co-rotating double screw extruder TSA EF 26-20. The cochlea of the feeding hopper is in position III, while the extruder cochlea is rotated at 125 rpm. Simultaneously a solution is fed including demineralized water and isopropyl alcohol in proportion 4:1 w/w by means of a peristaltic pump Watson-Marlow at about 20 g/min. The product is extruded with a 0.4 mm axial die. The total extrusion time is 102 minutes. Immediately after the extrusion, the product is spheronized with a spheronizer Glatt P-50 with rotating speed of 750 rpm for 3 minutes. The so obtained pellets are desiccated in thermostatic furnace at 35° C. for 15 hours. The theoretical titer of the pellets, calculated by the composition, is 16.25 U-FIP/mg. The obtained lipase titer was, on the contrary, 0 U-FIP/mg. It is supposed that the lipase is degraded (100% activity loss) because of the process conditions (overheating of the product and/or presence of water in the extruded mass).

Further reference experiments made by the Applicant, did not highlight any better results: the wet granulation produces pellets with irregular surface requiring too high quantity of gastroresistant coating polymers; the application of pancreatin on pancreatin pellets (in fluid bed with rotating disc Glatt GPCG-1 with insertion Rotor "tangential spray") is a too long process, with frequent stoppage of the filter hoses, and with difficulty in controlling the microspheres sizes.

Example 3

Preparation of Pancreatin Pellets Through Direct Spheronisation in Fluid Bed 680.0 g of pancreatin and 320.0 g of PEG400 (polyethylene glycol) are placed in the basket of a fluid bed Glatt GPCG-1 provided with Rotor insertion. The disc is of the knurled type and revolves at 1200 rpm, while simultaneously air is blown at 70° C. at about 1-2 m/sec. The filter hoses are shaken for 5 sec any 6 sec. After 60 minutes spheronisation the entering air temperature is lowered to 20° C. to obtain the hardening of the pellets, while the disc rotation keeps on at 700 rpm. In this stage the shaking of the filters is of 5 sec any 12 sec. After about 30 min cooling the product is unloaded from the basket of the fluid bed. The process total time is 90 minutes. The theoretical titer of the pellets, calculated by the composition, is 40.12 U-FIP/mg. The obtained enzymatic titer (lipase) is 38.12 U-FIP/mg, with an activity loss lower than the 5%.

In all test the ponderal yield of pellets having sizes between 150 μm and 700 μm was measured (Table 1). With the same perceptual compositions, by increasing the disc rotation speed, it was possible to reduce the spheronisation time, whereas the diameter of the microspheres did not change remarkably (Table 2).

Example 4

Preparation of Pancreatin Pellets Through Direct Spheronisation in Mixer-granulator 717.8 g of pancreatin and 190.8 of PEG4000 (polyethylene glycol) are placed in the tank of an high energy mixer-granulator Zanchetta Rotolab. The blades of the machine are run at 900 rpm and the heating jacket is set at 75° C. After 45 minutes spheronisation the heating is switched off, the blades speed is lowered to 120 rpm and the jacket is cooled through pipe water flow. After 15 minutes cooling the pellets are unloaded. The process total time is 60 minutes. The theoretical titer of the pellets, calculated by the composition, is 65.87 U-FIP/mg. The obtained enzymatic title titer (lipase) is 67.80 U-FIP/mg.

Using the described process, with a mixer-granulator Zanchetta Rotolab P-50 spherical pellets are obtained which are afterwards coated with a gastroresistant membrane formed by HP-55, triethylcitrate and talc. The coated pellets are wrapped up in thermo-sealed sachets (formed by a triple layer of paper, aluminum and polyethylene) and subjected to stability test at 25° C.+60% UR and at 30° C.+60% UR. The stability results of two lots made according to this process, expressed in percentage residual lipase activity, are reported in FIG. 1: it is to notice that the microsphere enzymatic activity remains substantially unchanged (fluctuating in a range of 90-110% of the initial value) during the whole test time (6 months).

In short, the data of the above reported examples show that, while the known processes (reference examples 1-2) bring to a substantial reduction in the enzymatic activity, the process object of the present invention (examples 3-4) allows to obtain microspheres having very small sizes (<700 μm) and an enzymatic titer 95 to over 100% than the native enzyme, thus substantially unchanged; the stability in time of these values is confirmed by the data in FIG. 1. Said results then highlight the unforeseen efficiency of the process of the present invention and the better performance of the microspheres so obtained. Further tests have been made in the condition of the example 3, changing the hydrophilic low melting polymer concentration and the disc rotation speed. The table 1 and 2 show the process yield. The PEG concentration is measured as weight rate of PEG with respect to the starting mixture; the process yield is calculated as weight rate (with respect to the starting mixture) of the microspheres fraction having dimensions included between 150 and 700 μm.

TABLE 1

| PEG (%) | ROTATION SPEED (RPM) | PROCESS YIELD (WEIGHT % 150-700 μM) |
|---|---|---|
| 20 | 700 | 48.9 |
| 25 | 700 | 58.1 |
| 30 | 700 | 80.6 |
| 32 | 700 | 91.8 |

Increasing the disc rotation speed to 1200 rpm (table 2) the yield values are not remarkably changed, while it has proved possible to reduce of 10-15% the process total time, to advantage of the enzyme stability.

TABLE 2

| PEG (%) | ROTATION SPEED (RPM) | PROCESS YIELD (WEIGHT % 150-700 μM) |
|---|---|---|
| 20 | 1200 | 41.6 |
| 25 | 1200 | 47.9 |
| 30 | 1200 | 83.3 |
| 32 | 1200. | 90.8 |

The invention claimed is:

1. Microspheres comprising one or more pancreatic enzymes, one or more hydrophilic low melting polymers, and optionally excipients, the ratio between said one or more pancreatic enzymes and said one or more hydrophilic low melting polymers is between 4:1 and 1:1, said microspheres having diameter comprised between 10 μm and 1500 μm and enzymatic titer equal to or higher than 90% of the titer of the solid mixture of their components.

2. Microspheres according to claim 1, having diameter comprised between 100 μm and 800 μm and enzymatic titer equal to or higher than 95% of the titer of the solid mixture of their components.

3. Microspheres according to claim 1, where said hydrophilic polymer has melting point between 20° C. and 90° C.

4. Microspheres according to claim 1, where said hydrophilic polymer has melting point between 30° C. and 70° C.

5. Microspheres according to claim 1, comprising between 15% and 40% w/w of said hydrophilic polymer and between 60% and 85% w/w of said pancreatic enzymes.

6. Microspheres according to claim 1, where said hydrophilic polymer is selected from polyethylene glycol, polyoxyethylene, copolymers of polyoxyethylene and polyoxypropylene or mixtures thereof.

7. A pharmaceutical composition comprising microspheres of claim 1, and pharmaceutically acceptable excipients, wherein the composition is optionally coated with a polymeric film.

8. The composition of claim 7 in form of powder, pellets, hard or soft gelatine capsules, tablets, microtablets, solutions or suspensions.

9. The composition of claim 7, wherein one or more pancreatic enzymes is present in weight rate between about 40% and about 99% and one or more hydrophilic low melting polymers is present in weight rate between about 1% and 60%.

10. A dosage form comprising the pharmaceutical composition of claim 7.

11. The dosage form of claim 10, wherein one or more pancreatic enzymes is present in weight rate between about 40% and about 99% and one or more hydrophilic low melting polymers is present in weight rate between about 1% and 60%.

12. A method of treating a disease condition, comprising administering the composition of claim 7 to a patient in need thereof.

* * * * *